(12) United States Patent
Errico et al.

(10) Patent No.: US 6,558,387 B2
(45) Date of Patent: May 6, 2003

(54) POROUS INTERBODY FUSION DEVICE HAVING INTEGRATED POLYAXIAL LOCKING INTERFERENCE SCREWS

(75) Inventors: Thomas J. Errico, Summit, NJ (US); James D. Ralph, Oakland, NJ (US); Joseph P. Errico, Far Hills, NJ (US)

(73) Assignee: Fastemetix, LLC, Summit, NJ (US)

( * ) Notice: Subject to any disclaimer, the term of this patent is extended or adjusted under 35 U.S.C. 154(b) by 40 days.

(21) Appl. No.: 09/844,904

(22) Filed: Apr. 27, 2001

(65) Prior Publication Data

US 2002/0103487 A1 Aug. 1, 2002

Related U.S. Application Data

(63) Continuation-in-part of application No. 09/774,915, filed on Jan. 30, 2001.

(51) Int. Cl.⁷ .............................................. A61B 17/70
(52) U.S. Cl. ..................... 606/61; 606/69; 606/70; 606/71; 606/72; 606/61; 606/103; 623/17; 623/17.11; 623/22; 623/66
(58) Field of Search ............... 606/69, 70, 71, 606/72, 61; 623/17, 17.11, 22, 66

(56) References Cited

U.S. PATENT DOCUMENTS

| | | | | |
|---|---|---|---|---|
| 4,805,602 A | * | 2/1989 | Puno et al. ............... | 24/135 N |
| 4,820,305 A | * | 4/1989 | Harms et al. ................. | 606/61 |
| 4,904,261 A | * | 2/1990 | Dove et al. ............... | 623/17.16 |
| 5,176,678 A | * | 1/1993 | Tsou ........................... | 606/53 |
| 5,258,031 A | * | 11/1993 | Salib et al. .................... | 606/61 |
| 5,522,899 A | * | 6/1996 | Michelson ................... | 606/61 |
| 5,653,762 A | * | 8/1997 | Pisharodi ..................... | 606/60 |
| 5,702,449 A | * | 12/1997 | McKay ..................... | 623/17.16 |
| 5,904,688 A | * | 5/1999 | Gilbert et al. ................ | 606/81 |
| 6,066,174 A | * | 5/2000 | Farris .......................... | 606/206 |
| 6,066,175 A | * | 5/2000 | Henderson et al. ...... | 623/17.11 |
| 6,099,531 A | * | 8/2000 | Bonutti ....................... | 606/87 |
| 6,248,106 B1 | * | 6/2001 | Ferree ......................... | 606/61 |
| 6,355,038 B1 | * | 3/2002 | Pisharodi .................... | 411/538 |
| 6,358,254 B1 | * | 3/2002 | Anderson ................... | 606/103 |

* cited by examiner

Primary Examiner—Timothy L. Maust
Assistant Examiner—Azy Kokabi
(74) Attorney, Agent, or Firm—Joseph P. Errico, Esq.; Timothy J. Bortree, Esq.

(57) ABSTRACT

A porous metal intervertebral spacer having at least one angled through hole extending from the side of the implant to a surface which interfaces with a vertebral body end plate such that an interference screw may be driven through the implant and into the bone, thereby securing the implant from undesired motion. In particular, the through holes are tapered to receive a screw and coupling element therethrough such that once fully seated, the screw is locked to the implant by virtue of a coupling element-through hole mutually tapered nesting. The head of the screw is round, as is the interior of the coupling element, thereby allowing the screw to be inserted at various angles relative to the hole without interfering with the proper seating of the coupling element in the through hole.

14 Claims, 3 Drawing Sheets

POROUS INTERBODY FUSION DEVICE HAVING INTEGRATED POLYAXIAL LOCKING INTERFERENCE SCREWS

CROSS REFERENCE TO RELATED APPLICATION

This application is a continuation-in-part of Reissue application Ser. No. 09/774,915 entitled "A Polyaxial Pedicle Screw Having a Threaded and Tapered Compression Locking Mechanism", filed Jan. 30, 2001.

BACKGROUND OF THE INVENTION

1. Field of the Invention

This invention relates generally to a spinal implant device for implantation into the intervertebral space between adjacent vertebral bones to potentiate fusion, and more particularly to an implantable device having superior stability provided by polyaxial locking interference screws.

2. Description of the Prior Art

The bones and connective tissue of an adult human spinal column consists of more than twenty discrete bones coupled sequentially to one another by a tri-joint complex which consists of an anterior disc and the two posterior facet joints, the anterior discs of adjacent bones being cushioned by cartilage spacers referred to as intervertebral discs. These more than twenty bones are anatomically categorized as being members of one of four classifications: cervical; thoracic; lumbar; or sacral.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, and the insertion of implants and/or height restorative devices, several methods and devices have been disclosed in the prior art.

More particularly, and with respect to the historical development of the present surgical methods and instrumentations, the description of the relevant medical techniques are now described. Failure of the intervertebral disc cartilage generally includes a loss of proper anatomical spacing between the end plates of the opposing vertebral bodies. This loss of height may simply destabilize the spine, or, in severe cases, it may cause considerable neurological impairment as the nerve roots are compressed by the converging lateral extensions of the bones (e.g. in the facet joint).

Restoring the appropriate height to the intervertebral space is the first step in the surgical strategy for correcting this condition. Once this is achieved, one class of surgical implantation procedures involves positioning a device into the intervening space. This may be done through a posterior approach, a lateral approach, or an anterior approach. Various implant devices for this purpose include femoral ring allograft, cylindrical metallic devices (i.e., cages), and metal mesh structures that may be filled with suitable bone graft materials. Some of these implant devices are only suitable for one direction of approach to the spine. All of these devices, however, are provided with the intention that the adjacent bones will, once restored to their appropriate separation, then grow together across the space and fuse together (or at least fuse into the device implanted between the bones).

Most recently, the development of non-fusion implant devices, which purport to permit continued natural movement in the tri-joint complex have provided great promise. The instrumentation and methods for the implantation of these non-fusion devices, as well as the implantation of the fusion devices catalogued previously, therefore should integrate the functions of restoring proper anatomical spacing and easy insertion of the selected device into the formed volume.

To these ends, several instruments for such implantation have been described in the prior art. These include U.S. Pat. No. 6,159,215 to Urbahns, et al., U.S. Pat. No. 6,042,582 to Ray, and U.S. Pat. 5,431,658 to Moskovich. More particularly, the U.S. Patent to Ray describes a device and method of implantation for use specifically with cylindrical cage devices which are inserted such that the axis of the implant device is perpendicular to the axis of the spine. The reference teaches the use of a series of similarly shaped plugs to be inserted posteriorly between the collapsed bones, for the purposes of separating the adjacent bones, followed by the cutting of the end plates to receive the threaded implant.

The Urbahns, et al. reference (U.S. Pat. No. 6,042,582) teaches the use of intervertebral space measuring tools and a spacer insertion device for facilitating the implantation of an intervertebral spacer (in this reference, the spacer implant is a tubular metal mesh structure which is coaxial with the patient's spine). The measuring device described in this reference (and shown in FIG. 4) comprises a thin, elongate rod having a fixed cylindrical end having a constant and known thickness. Insertion of this measuring tool into the intervertebral space provides the physician with an approximate understanding of the size of the implant to be inserted. This measurement defines the appropriate cutting of the patient's bone to create the desired, and necessary, space to receive the metal mesh. The measuring tool is, however, not used to distract the space.

This distraction is provided in conjunction with the spacer insertion instrument shown in FIGS. 13–16. This facilitator, which is more fully described in U.S. Pat. No. 5,431,658 (FIG. 4, thereof), comprises a pair of flat elongate guide surfaces which are hinged at an elbow joint at the distal ends of the surfaces. The distal joint is designed to extend out of the planes defined by the longitudinal axes of the two guides. The proximal ends of the surfaces are to be placed between the collapsed bones. By virtue of the elbow joint, the surfaces are angled substantially when the metal mesh structure, or test member, is placed between the surfaces. The metal mesh (or the test member) is then hammered down the guide surfaces, prying the bodies apart. U.S. Pat. No. 5,431,658, to Moskovich, which was referenced above in the description of the patent to Urbahns, is generally directed to a threaded insertion device for final placement of the femoral ring (not a metal mesh structure) into the intervertebral space. A threaded shaft, having a distal ram portion and an intermediate nut, is coupled to the guide surfaces via stud-groove interfaces that engage studs on the intermediate nut and corresponding grooves on the elongate guide surfaces. The ram portion seats against the femoral ring and causes it to move relative to the guides. The space into which the femoral ring is to be inserted (as above with the metal mesh implant) must be cut to the appropriate size to receive the graft. Initially the surgeon rotateably advances the graft into the space. Subsequent to proper placement of the graft, i.e. when the graft jams into the pre-cut receiving space, continued rotation of the shaft causes the distraction surfaces to be removed by relative motion of the guides to the shaft (the intermediate nut engages the guides and puls them free of the vertebral bones). Failure to properly cut the space, or structural failure of the graft and/or bone material, will prevent removal of the guides, and further rotation of the shaft will drive the allograft further than clinically desired (risking paralysis and/or damage to surrounding vessels).

Referring now to the implant device itself, the substantial drawbacks of cage devices, including, but not limited to: 1. their failure to induce or accept robust ingrowth of bone for the development of a fusion; and 2. their susceptibility to sudden rotational instability, have led to their decreased usage. Correspondingly, the development of various other fusion and non-fusion implant devices has gained momentum. In the interim, however, the use of the classical fusion material, that is femoral ring allograft, has become the standard again. The proper porosity of the allograft bone makes it a superior fusion material, however, simple compression between the adjacent bones (often aided by the tension band of the remaining annulus material) is often not deemed sufficient to prevent dislocation of the implanted ring.

A method of stabilizing the implanted femoral ring allograft, which has gained usage is for the surgeon to insert an interference screw into the endplate of one of the vertebral bones, the extended head of which prevents the femoral ring from translating anteriorly. While effective, this stabilization technique does not entirely prevent movement of the allograft material, and thus does not prevent fusion inhibiting translating events.

It is, therefore, an important feature of the present invention that it provides superior stabilization for use in conjunction with femoral ring allograft material.

It is, however, the main feature of the present invention that it provides a superior fusion promoting implant device that can be completely stabilized in the intervertebral space.

Other featured functionalities of the present invention not explicitly stated will be set forth and will be more clearly understood in conjunction with the descriptions of the preferred embodiments disclosed hereafter.

SUMMARY OF THE INVENTION

The present invention comprises a porous metal implant device, shaped to seat in the distracted space between two vertebral bodies, and at least one polyaxial locking screw which maybe inserted through a corresponding hole in the implant, and into the adjacent bone. The polyaxial locking screws are designed to be inserted through the implant and into the bone within a range of angles, but are further designed with a head member that will lock within the hole of the implant. By locking to the implant itself, the screws minimize the possibility of implant or screw translation, and thereby maximize fusion rates.

Alternatively stated, the present invention generally comprises an intervertebral spacer device and locking interference screw assembly which includes a disc-shaped member having a circumferential side surface, and upper and bottom end surfaces. The disc-shaped member includes at least one through hole extending from this side surface through one of said end surfaces. At least one screw is also included, which screw is insertable through the at least one through hole. The head portion of the screw is designed to lock within its corresponding through hole.

The head portion of the screw or screws are encompassed within a hollow interior of a coupling element so that both initially remain selectively rotationally mounted to one another. The coupling element may include a slot that permits the interior volume to open and close around the head of the screw.

In preferred embodiments, the through hole and the coupling element are tapered so that they crush lock together when the coupling element is seated into the through hole.

The disc-shaped member preferably comprises a porous material for permitting bony ingrowth (i.e. promoting fusion across the intervertebral space). It is further anticipated that the upper and bottom end surfaces of the disc-shaped member are to be convex, thus shaping themselves to the end plate bone surfaces of the vertebral bodies.

More particularly with respect to the spacer member itself, the device is formed of a porous material, for example bone allograft material or metal. In the present embodiment, a porous titanium metal mesh, having pore sizes ranging from 100 to 500 microns, is desirable. The shape of the implant, as suggested above, should be ideally formed to fit within the anatomical space provided between the endplates of adjacent vertebral bones. In particular, the upper and lower surfaces should be convex, and the perimeter should be approximately oval. This shape provides for more distributed loading of pressure, which in turn, facilitates bone ingrowth into the matrix of the micromesh.

The implant device is further designed with a series of tapered macroscopic holes which extend from the anterior or lateral face (the side of the implant which, once implanted, is directed toward the front of the spine) through to the upper surface (or alternatively through the lower surface).

The screws of the present invention comprise standard threading and shaft portions. The head, however, is not standard in that it comprises a semi-spherical section. The semi-spherical head of the screw seats within a collet, or coupling member, which is exteriorly tapered and seats in the tapered holes of the implant member. The interior surface of the collet element is correspondingly semi-spherical so that the screw may be implanted polyaxially through the hole, but that the collet will seat in the hole without an angulation relative to the true axis of the hole.

More particularly, the coupling element comprises a socket for holding the ball head of the screw, and an exterior tapered surface which mates with the tapered holes of the plate. In the principle variation, the coupling element includes an axial slot that is forced closed upon insertion into the hole in the plate. Forced closure of the collet, by compression within the tapered hole thereby locks the ball to the coupling element. In another variation, only the lower portion of the collet includes a slot (in this variation, preferably a plurality of slots) for locking the ball head to the coupling element and to the porous spacer implant. In both variations it is preferable for the coupling elements to be tapered so that insertion into the hole locks the ball to the coupling elements.

Specifically, with respect to the method of implantation of this spacer device, the following is a desirable surgical protocol for the insertion and securement of the present invention. After exposing the collapsed disc space, the surgeon removes the damaged cartilage, and distracts the adjacent bones to the desired and proper distance (height), and then inserts the porous spacer of the present invention into the volume that has been created. An insertion tool, which would be ideal for placing the spacer in the proper position, is described more fully in copending application, U.S. Ser. No. 10/076,688, to James D. Ralph and Stephen Tatar, entitled "Femoral Ring Loader", the specification of which is incorporated herein by reference.

Once the spacer of the present invention is properly positioned, the surgeon inserts the screws through the holes at the desired angle and drives it into the adjacent bone. Complete insertion of the crew causes the coupling member (the collet) to slide into the tapered hole of the spacer and to lock therein, independent of the angulation of the screw (within a range of angles). This secures the spacer implant in the appropriate position. The ability to angulate the screw is a significant advantage. The ability to angulate the screws while simultaneously having the heads of the screws locked to the spacer is the principle advantage of the present invention, which is described in particular preferred embodiments hereinafter, with reference to the included Figures.

DETAILED DESCRIPTION OF THE PREFERRED EMBODIMENTS

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1A:
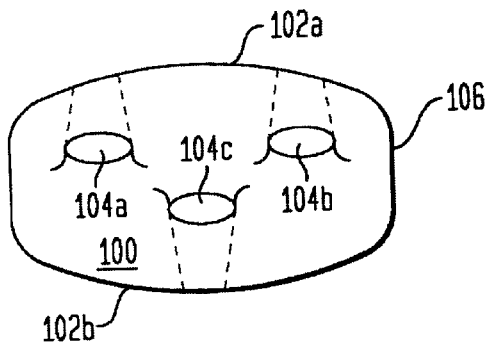
FIGS. 1a–c are side, top, and bottom views of one embodiment of a porous intervertebral spacer which is an aspect of the present invention.
Figure 1B:
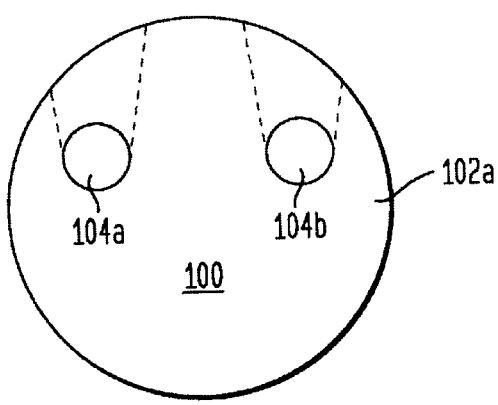
Figure 1C:
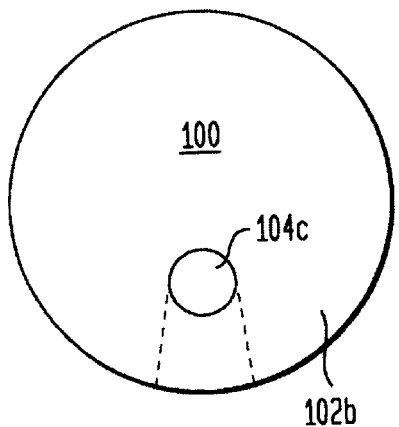

Referring now to FIGS. 1a–c, a porous metal intervertebral spacer device 100 is provided in side, top and bottom views, respectively. The device is disc shaped, having a diameter that is approximately eighty percent of the diameter of the end plates of the adjacent vertebral bodies. This permits a greater portion of the end plates of each bone to seat directly on the spacer, distributing the load more effectively over the implant (and promoting more natural loading on the bone, which loading alone has been shown to stimulate bone growth). In order to enhance this effect even more, the upper and lower surfaces 102a, 102b of the spacer 100 are convex, approximating the concavity of the bone end plates.

For similar reasons, the height of the spacer 100 is designed to fit snugly in the space between the two distracted vertebral bodies. This is achieved by distracting instruments and spacer insertion tools, of the type more fully described hereinbelow with respect to FIG. 4. In as much as the appropriate anatomical separation of the end plates varies among the populations and along the spinal column various spacers 100 of different thicknesses will be produced.

The spacer device 100 further includes a plurality of tapered holes 104a–c which extend fully through the spacer 100, from the peripheral surface 106 to the top surface 102a (or bottom 102b). The holes 104a–c are slightly tapered such that the slightly narrower ends are located at the upper surface 102a (or lower surface 102b). These tapered holes 104a–c are designed to receive, therethrough, the combined screw and coupling elements as more fully described below with respect to FIGS. 2 and 3. In as much as the holes 104a–c are necessarily angled through the edge of the spacer, the openings 108a–c of the holes on the peripheral surface are recessed so that the screw an coupling element combination may pass through the device without binding.

Figure 2:
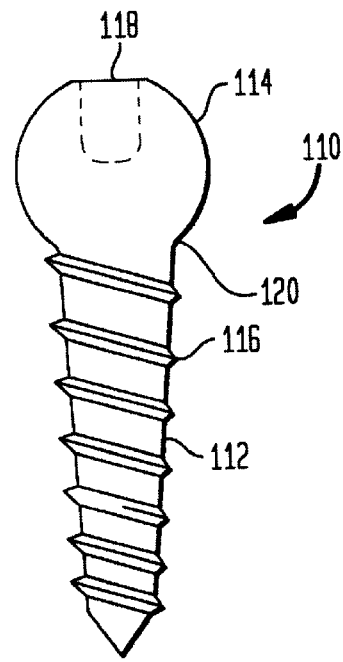
FIG. 2 is a side view of a polyaxial bone screw that is an aspect of the present invention.

More particularly, now with respect to the screw 110, which is shown in a side view in FIG. 2, the screw 110 comprises a simple threaded shaft 112, and a semi-spherical head 114. The shaft 112 is shown as having a tapered shape with a high pitch thread 116. It shall be understood that a variety of shaft designs are interchangeable with the present invention. The specific choice of shaft features, such as thread pitch, or shaft diameter to thread diameter ratio, or overall shaft shape, etc. should be made by the physician with respect to the conditions of the patient's bone, however, this invention is compatible with a wide variety of shaft designs.

The head portion 114 of the screw 110 comprises a semi-spherical shape, which has a recess 118 in it. It is understood that the semi-spherical shape is necessarily a section of a sphere, greater in extent than a hemisphere, and is defined by an external surface which is equidistant from a center point of the head.

The recess 118 defines a receiving locus for the application of a torque for driving the screw 110 into the bone. The specific shape of the recess 118 may be chosen to cooperate with any suitable screwdriving tool. For example, the recess 118 may comprise a slot for a flat-headed screwdriver, a crossed recess for a phillips head screwdriver, or most preferably, a hexagonally shaped hole for receiving an allen wrench. It is further preferable that the recess 118 be co-axial with the general elongate axis of the screw 110, and most particularly with respect to the shaft 112. Having the axes of the recess 118 and the shaft 112 co-linear facilitates step of inserting the screw 110 into the bone.

The semi-spherical head portion 114 is connected to the shaft 112 at a neck portion 120. While it is preferable that the diameter of the shaft 112 be less than the radius of the semi-spherical head 114, it is also preferable that the neck 120 of the screw 110 be no wider widest portion of the shaft 112. This preferable dimension permits the screw to be inserted into the bone at a variety of angles while still permitting the coupling element (to be described with respect to FIG. 3) to be lockably mated with the elongate hole into which the screw and coupling element are inserted, while remaining coupled to the head 114.

Figure 3:
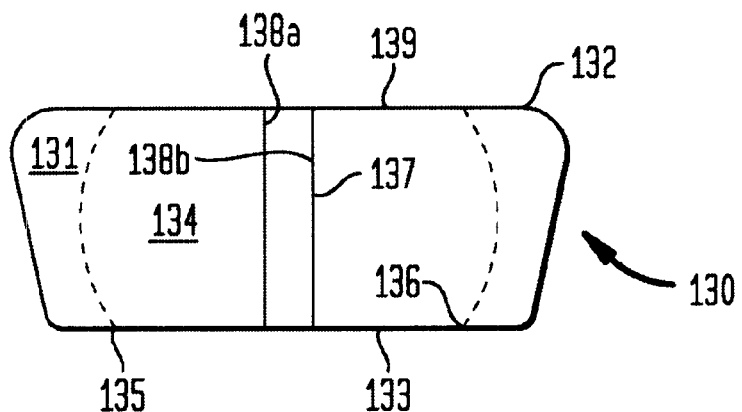
FIG. 3 is a side view of a coupling element that is also an aspect of the present invention.

Referring now to FIG. 3, a coupling element 130 of the preferred embodiment of the present invention is shown in a side view, wherein phantom lines correspond to internal features of the coupling element. The coupling element 130 comprises a generally cylindrical body 131, having a tapered axial length, wherein the diameter of the top 132 of the element is wider than the bottom 133 of the element. The interior of the coupling element 130 comprises semi-spherical volume 134 which is ideally suited for holding the head portion 114 of the screw 110, and permitting the screw to rotate through a range of angles. The bottom 133 of the coupling element 130 has a has a circular hole (enumerated as 135 on the bottom surface 133 of the side view of the coupling element 130 in FIG. 2) which forms the bottom entrance into the interior semi-spherical volume 134. It is understood that the head 114 of the screw 110 is held within the interior semi-spherical volume 134 by an annular rim, or support lip, 136 of the bottom 133 of the coupling element 130. This annular support lip 136 defines the circular opening 135 which has a diameter less than the diameter of the semi-spherical head 114 of the screw 110.

It is, therefore, preferred that the coupling element 130 include an axial slot 137 which extends the entire length of the element 130. This slot interrupts the circumferential continuity of the outer periphery of the element, and extends approximately radially outward from the inner surface of the volume 134. The head 114 of the screw 110 can be inserted into the inner volume of the coupling element by expansion of the axial slot 137 via application of force against the inner surfaces 138a, 138b of the slot 137. Forced insertion of this coupling element into a hole tapered, such as the tapered holes 104a–c of the spacer 100, which taper provides a radial closing force to the slot 137 which drives the inner surfaces 138a, 138b of the slot 137 together, therein causing the interior volume 134 to shrink and the coupling element 130 to lock to the screw head 114 under compression pressure.

The top 132 of the coupling element 130 further comprises a through hole 139, which extends from the top surface 132 to the interior semi-spherical volume 134. This through hole 139 is designed such that the screwdriving tool that is used to insert the screw 110 into the bone may access and rotate the screw 110 through the coupling element 130.

The coupling elements 130 of this invention are, therefore, designed to fit into the sloped and tapered elongate holes 104a–c of the spacer 100. The insertion of the screws 110 coupled with their corresponding coupling elements 130, through the spacer 100 and into the end plate of the vertebral bone, followed by continued driving of the screws 110 into the bone, causes the coupling elements 130 to travel down the slope of their corresponding tapered holes 104a–c, therein moving the coupling element 130 relative to the hole. Once the coupling elements have each fully seated, the continued movement applies a compressive force, therein locking the ball heads 114 of the screws 110 to the coupling elements 130, and the coupling elements 130 within the holes 104a–c.

Figure 4:
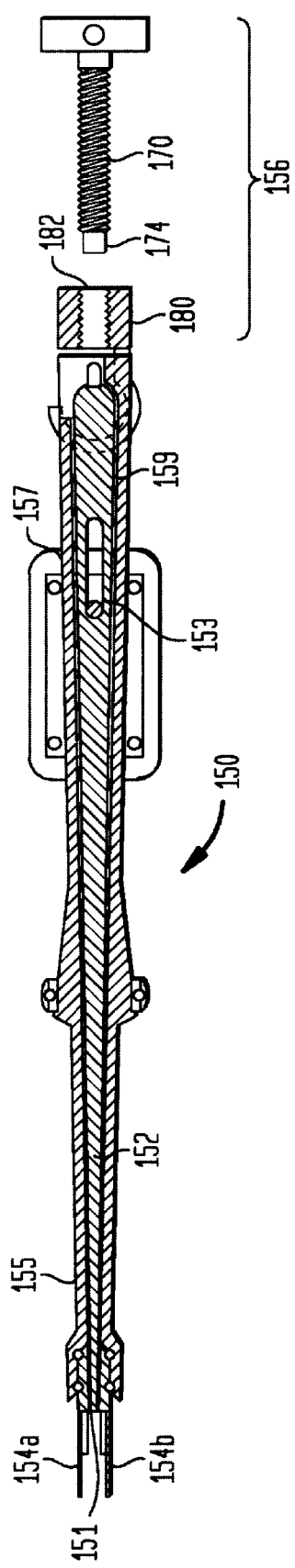
FIG. 4 is a side perspective illustration of a spacer insertion tool which may be used in conjunction with various implants, including the present invention.

Referring now to FIG. 4, an instrument for inserting intervertebral spacer devices, such as the present invention, between adjacent vertebral bodies is provided in a side perspective view. More particularly, the insertion tool 150 includes a guard/holder element 152, a retractor element 155, a selectively rotateable threaded pin 170, and a curved forked member 180 which includes a threaded bore.

More specifically, with respect to the guard/holder member 152, it comprises an elongate shaft having a distal end 151 which is adapted to hold the spacer element during insertion between the vertebral bodies, and a proximal end 159 which includes a pair of oppositely oriented laterally extending knobs 153. This guard/holder 152 may be designed to selectively grip a surface structure of the spacer, or as in conjunction with the preferred embodiment, the holder may couple to the tapered holes of the implant.

In addition, the insertion tool 150 comprises a tubular retractor element 155. The retractor comprises a hollow bore, in which the guard/holder 152 may slideably translate. The knobs 153 of the guard/holder 152 seat in grooves in the proximal end 157 of the retractor element 155. This engagement prevents the two elements from fully separating, but permits relatively unconstrained translation of the guard/holder shaft 152 in the tubular body of the retractor 155.

The retractor 155 further includes a pair of distally mounted retractor surfaces 154a–b which are provided to hold the vertebral bones apart.

A retractor withdrawal mechanism 156, which is comprised of the selectively rotateable threaded plunger element 170, and the curved forked member 180 which includes a threaded bore portion 182, is provided to withdraw these retractor surfaces 154a–b away from the spine after the insertion of the spacer. More particularly, the curved forked member includes a pair of curved claws that engage and hold the retractor 155. The upper portion 182 of the forked member 180 is a threaded bore which engages the threaded plunger element 170.

In the initial conformation, the guard/holder 152 and the retractor member 155 are held in locked position by the forked member 170. Once the spacer 100 is inserted, however, the forked member 170 is rotated into a position that aligns the threaded bore into a coaxial position relative to the guard/holder 152 shaft. Rotation of the threaded plunger member 170 brings the end 174 of the plunger into contact with the proximal end 159 of the guard holder 152. Continued rotation forces the retractor 155 and the guard/holder 152 elements to move relative to one another, and more specifically, for the retractor surfaces 154a–b to slide free of the vertebral bodies as the guard/holder 152 prevents the spacer from sliding out of its proper position in the intervertebral space.

During implantation of the present invention, the surgeon first prepares the intervertebral space for insertion of the spacer. This generally includes the removal of any cartilage fragments or other tissue that may be trapped in the collapsed intervertebral space. The surgeon then expands the space between the vertebral bodies enough to accommodate the spacer that is to be inserted. This expansion is generally measured by surgeon experience, but is also determined by the restoration of anatomically appropriate tension in the remaining annulus material surrounding the space. This tension is very useful in helping to hold the spacer in the intervertebral volume as the fusion begins to form through the porous material of the present invention.

The surgeon then operates the instrument to hold the spacer 100 between the retraction surfaces 154a–b, and at the distal end 151 of the guard/holder element 152. The spacer 100 is then positioned between the vertebral bodies. The surfaces of the distal retractor ends are micromachined to be extremely smooth so that the insertion can be accomplished with the minimum force necessary and with a minimum of collateral damage. The curved forked member 180 is then swung into position and the threaded plunger 170 is engaged to withdraw the retractor surfaces 154a–b.

Figure 5:
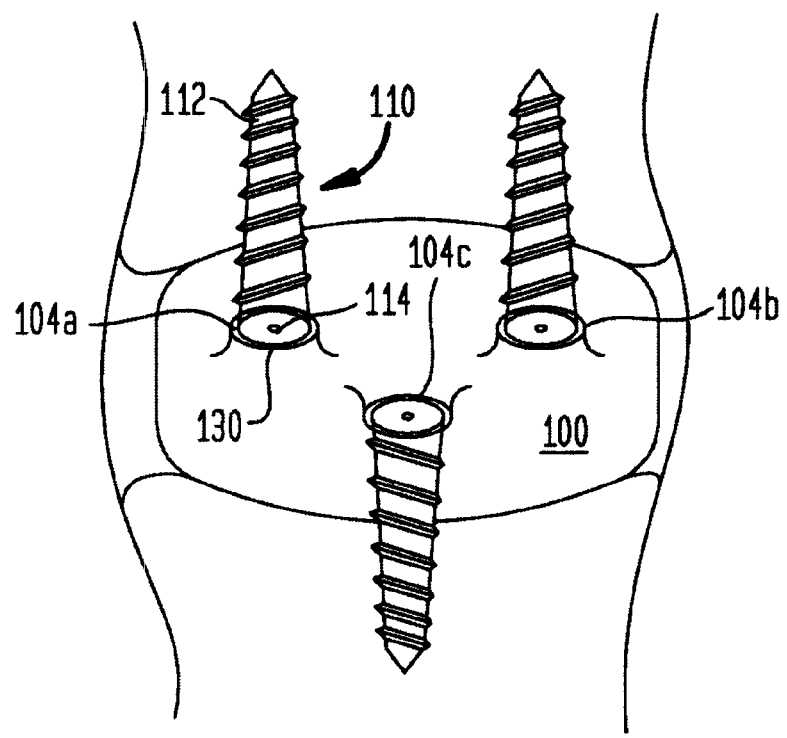
FIG. 5 is a side view of a spacer of the present invention implanted between adjacent vertebral bodies, and secured therebetween by polyaxial locking interference screws and coupling elements of the type illustrated in FIGS. 2 and 3.

With reference now to FIG. 5, the insertion and locking of the polyaxial interference screws is described. In most instances, the coupling elements 130 are already preloaded onto the semi-spherical heads 114 of the screws 110, however, there are embodiments contemplated in which the screw shaft 112 can pass through the center of the coupling element 130 which receives the head of the screw when it reaches the element 130 in the hole 104. In either event, with the spacer 100 properly positioned, the surgeon drives the screws 110 through the holes 104a–c of the spacer 100 and into the end plates of the adjacent bones. The nature of the polyaxial screw and coupling element interface permits the screws to be inserted within a range of angles, which particular angle to be used being selectable by the surgeon.

More particularly, once the screw has been inserted into the bone, at the desired angle, the coupling element 130, via its rotationally free mating of the socket 134 to the head 114 of the screw 110, is realigned so that it may be seated against the tapered surfaces in the tapered hole 104a–c. Continued rotation of the screw 110, therefore, causes the coupling element 130 to slide deeper into the hole, which correspondingly requires that the screw 110 and coupling element 130 to move relative to the spacer 100. The coupling element 130 continues to slide down the ever narrowing tapered walls of the hole, until it causes the slot 137 to close, therein crush locking the coupling element 130 to the screw head 114, and further therein compression locking the coupling element 130 to the spacer 100.

What is claimed is:

1. An intervertebral spacer device and polyaxial locking interference screw assembly, comprising:
    a disc-shaped member having a circumferential side surface, an upper surface, and a bottom surface, said disc shaped member including at least one through hole, each of said at least one trough hole extending from the circumferential side surface to at least one of the top and bottom surfaces;
    at least one screw, said screw including a semi-spherical head; and
    at least one corresponding coupling element, said coupling element including an interior semi-spherical volume,
    which at least one corresponding coupling element is mountable onto said corresponding head of said screw such that said screw and said coupling element pair may freely rotate relative to one another, and
    which coupling element and screw pair are insertable into and partially through one of said at least one through hole of said disc-shaped member such that via said insertion, said coupling element locks within the corresponding through hole;
    wherein said at least one coupling element further comprises an axially aligned slot formed therein, which slot causes the interior semi-spherical volume to expand and contact in accordance with the application of suitable compressive loads applied to an exterior surface of said coupling element, such that a suitable compressive load causes the coupling element to crush onto the semi-spherical head of the corresponding at least one screw upon sealing of the coupling element in the corresponding through hole.

2. The intervertebral spacer device and polyaxial locking interference screw assembly as set forth in claim 1, wherein said disc-shaped member comprises a porous material.

3. The intervertebral spacer device and polyaxial locking interference screw assembly as set forth in claim 2, wherein said porous material is a porous metal material which forms a bone-like lattice microstructure.

4. The intervertebral spacer device and polyaxial locking interference screw assembly as set forth in claim 1, wherein said upper surface and said bottom surface of said disc-shaped member are convex.

5. The intervertebral spacer device and polyaxial locking interference screw assembly as set forth in claim 1, wherein said at least one through hole is tapered such that the portion of the through hole which is closest to the circumferential side surface is wider than the portion of the through hole which is farthest from the circumferential side surface.

6. The intervertebral spacer device and polyaxial locking interference screw assembly as set forth in claim 5, wherein said at least one corresponding coupling element includes an exterior taper which corresponds to the taper of the at least one through hole.

7. An intervertebral spacer device and polyaxial locking interference screw assembly, comprising:
    a disc-shaped spacer element having a set of at least two through holes disposed in spaced relation with respect to each other;
    at least one coupling element said coupling element being insertable into a corresponding through hole; and
    at least one corresponding bone screw, said bone screw having a semi-spherical head portion and a shaft, said semi-spherical head portion being rotationally coupled to the coupling element, and said shaft portion being insertable through the corresponding through hole and into a vertebral bone;
    wherein said coupling elements each comprise an interior semi-spherical volume, defined by a curved interior surface, which forms a receiving socket into which the semi-spherical portion head portion is inserted whereby the head portion of said screw is rotationally coupled to said coupling element; and
    wherein the curved interior surface of said coupling element further comprises at least one slot which permit the interior semi-spherical volume to expand thereby facilitating the insertion of said head portion of said screw therein.

8. The polyaxial locking screw and plate assembly as set forth in claim 7, wherein said at least one slot comprises a single slot which extends the axial length of the coupling element, therein defining the coupling element as an incomplete circular section.

9. The polyaxial locking screw and plate assembly as set forth in claim 7, wherein the corresponding through hole into which the coupling element is inserted is tapered inwardly, thereby causing, upon insertion of said coupling element into said corresponding through hole, the slots to be compressed, which causes the curved interior surface of the coupling element to lock the head portion of the screw at a definite insertion angle.

10. The polyaxial locking screw and plate assembly as set forth in claim 9, wherein the corresponding through hole into which the coupling element is inserted is tapered inwardly, thereby causing, upon insertion of said coupling element into said corresponding through hole, the single slot to compress together, and for said incomplete circular section to lock the head portion of the screw at a definite insertion angle.

11. An intervertebral spacer device and locking interference screw assembly, comprising:
    a disc-shaped member having a circumferential side surface, and upper and bottom end surfaces, said disc shaped member including at least one through hole extending from said side surface through one of said end surfaces;
    at least one screw, said screw being insertable through said at least one through hole, said screw further including a head portion,
    wherein said head portion locks to the at least one through hole;

wherein said head portion of said screw includes a coupling element and a semi-spherical portion, which is coupling is selectively rotationally mounted to the semi-spherical portion of said screw;

wherein said coupling element includes an exterior taper which corresponds to the taper of the at least one through hole, and wherein said coupling element includes an interior semi-spherical volume for containing the semi-spherical portion of the screw; and wherein said coupling element portion of the head of said screw further comprises an axially aligned slot formed therein, which slot causes the interior semi-spherical volume to expand and contract in accordance with the application of suitable compressive loads applied to art exterior surface of said coupling element such that a suitable compressive load causes the coupling element to crush onto the semi-spherical portion of the head of the corresponding at least one screw upon seating of the coupling element in the tapered through hole.

12. The intervertebral spacer device and locking interference screw assembly as set forth in claim 11, wherein said disc-shaped member comprises a porous material.

13. The intervertebral spacer device and locking interference screw assembly as set forth in claim 11, wherein said upper end surface and said bottom end surface of said disc-shaped member are convex.

14. The intervertebral spacer device and locking interference screw assembly as set forth in claim 11, wherein said at least one through hole is tapered such that the portion of the through hole which is closest to the circumferential side surface is wider than the portion of the through hole which is farthest from the circumferential side surface.

* * * * *